United States Patent [19]

Muller et al.

[11] 4,242,454

[45] Dec. 30, 1980

[54] FERMENTATION PROCESS

[75] Inventors: Werner C. Muller, Dobbs Ferry, N.Y.; Franklyn D. Miller, Cincinnati, Ohio

[73] Assignee: National Distillers and Chemical Corp., New York, N.Y.

[21] Appl. No.: 43,190

[22] Filed: May 29, 1979

[51] Int. Cl.³ .............................................. C12P 7/14
[52] U.S. Cl. ..................................... 435/162; 435/42; 435/813; 435/940
[58] Field of Search .............................. 435/161–165, 435/813, 940, 42

[56] References Cited

U.S. PATENT DOCUMENTS

| | | | |
|---|---|---|---|
| 2,419,960 | 5/1947 | Legg | 435/162 |
| 2,431,004 | 11/1947 | Wickerham | 435/162 X |
| 4,009,075 | 2/1977 | Hoge | 435/162 |

*Primary Examiner*—Lionel M. Shapiro
*Attorney, Agent, or Firm*—Kenneth D. Tremain

[57] ABSTRACT

A fermentable sugar feed is continuously converted by fermentation to dilute aqueous ethanol ("beer") in a series of agitated fermentation vessels which contain progressively more ethanol and less fermentable sugar. At least two strains of yeast are selected for the fermentation, one of which provides a high rate of ethanol production in a fermentation medium containing a relatively low concentration of ethanol and a relatively high concentration of fermentable sugar and the other of which provides a high rate of ethanol production in a fermentation medium containing a relatively high concentration of ethanol and a relatively low concentration of fermentable sugar.

11 Claims, 1 Drawing Figure

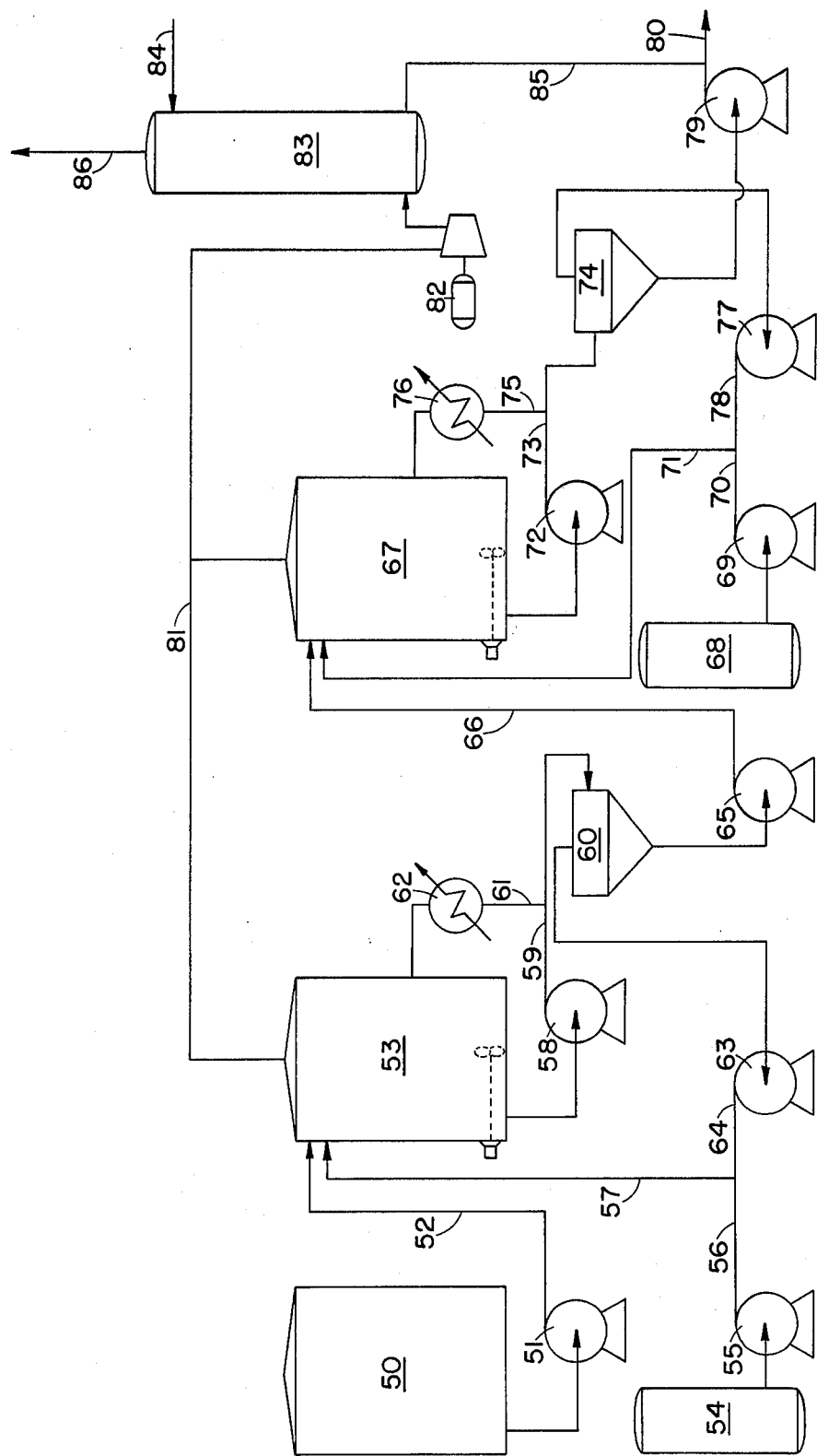

FERMENTATION PROCESS

CROSS REFERENCE TO RELATED APPLICATION

This application is related to commonly assigned copending U.S. patent application Ser. No. 43,193 filed May 29, 1979.

BACKGROUND OF THE INVENTION

1. Field of the Invention

This invention relates to processes for the manufacture of ethanol by fermentation.

2. Description of the Prior Art

With the ever-increasing depletion of economically recoverable petroleum reserves, the production of ethanol from vegetative sources as a partial or complete replacement for conventional fossil-based liquid fuels becomes more attractive. In some areas, the economic and technical feasibility of using a 90% unleaded gasoline-10% anhydrous ethanol blend ("gasohol") has shown encouraging results. According to a recent study, gasohol powered automobiles have averaged a 5% reduction in fuel compared to unleaded gasoline powered vehicles and have emitted one-third less carbon monoxide than the latter. In addition to offering promise as a practical and efficient fuel, biomass-derived ethanol in large quantities and at a competitive price has the potential in some areas for replacing certain petroleum-based chemical feedstocks. Thus, for example, ethanol can be catalytically dehydrated to ethylene, one of the most important of all chemical raw materials both in terms of quantity and versatility.

The various operations in processes for obtaining ethanol from such recurring sources as cellulose, cane sugar, amylaceous grains and tubers, e.g., the separation of starch granules from non-carbohydrate plant matter and other extraneous substances, the chemical and/or enzymatic hydrolysis of starch to fermentable sugar (liquefaction and saccharification), the fermentation of sugar to a dilute solution of ethanol ("beer") and the recovery of anhydrous ethanol by distillation, have been modified in numerous ways to achieve improvements in product yield, production rates and so forth. For ethanol to realize its vast potential as a partial or total substitute for petroleum fuels or as a substitute chemical feedstock, it is necessary that the manufacturing process be as efficient in the use of energy as possible so as to maximize the energy return for the amount of ethanol produced and enhance the standing of the ethanol as an economically viable replacement for petroleum based raw materials. To date, however, relatively little concern has been given to the energy requirements for manufacturing ethanol from biomass and consequently, little effort has been made to minimize the thermal expenditure for carrying out any of the discrete operations involved in the manufacture of ethanol from vegetative sources.

The substitution of alcohol for at least a portion of petroleum based fuels is particularly critical for developing economies where proven domestic petroleum reserves are limited, such as in India and Brazil and these nations have therefore increasingly emphasized the production of alcohol from vegetative sources. The most common such operation employs cane sugar in a fermentation-distillation operation which conveniently utilizes the bagasse by-product as a fuel source. Cassava or manioc (*Manihot utilissima Pohl*) as a source of starch has also been considered for conversion into alcohol (see "Brazil's National Alcohol Programme", Jackson, ed. *Process Biochemistry*, June 1976, pages 29–30; "Ethyl Alcohol from Cassava", Teixerira et al. *Industrial and Engineering Chemistry* pp. 1781–1783 (1950); and United Kingdom Pat. Specification No. 1,277,002). However, since manioc lacks the equivalent of sugar cane's bagasse, the fuel for alcohol conversion must come from an external source. Thus, to make manioc root an economically attractive source of ethanol, it is essential to achieve rapid and high levels of conversion of the starch content to fermentable saccharide and of the fermentable saccharide to ethanol with high levels of thermal efficiency and at conservative plant investment and operating costs.

Processes for the continuous fermentation of sugars to provide alcohol are well known (viz., U.S. Pat. Nos. 2,155,134; 2,371,208; 2,967,107; 3,015,612; 3,078,166; 3,093,548; 3,177,005; 3,201,328; 3,207,605; 3,207,606; 3,219,319; 3,234,026; 3,413,124; 3,528,889; 3,575,813; 3,591,454; 3,705,841; 3,737,323; and 3,940,492; "Process Design and Economic Studies of Alternative Fermentation Methods for the Production of Ethanol", Cysewski, et al. *Biotechnology and Bioengineering*, Vol. xx, Pp. 1421–1444 (1978). In a typical continuous fermentation process, a stream of sterile sugar liquor and a quantity of yeast cells are introduced into the first of a battery of fermentation vessels wherein initial fermentation takes place, generally under conditions favoring rapid cell growth. The partial fermentate admixed with yeast cells is continuously withdrawn from the first fermentation vessels wherein fermentation is carried out under conditions favoring the rapid conversion of sugar to ethanol. The yeast in the last fermentation vessel can be recovered by suitable means, e.g., centrifugation or settlement, and recycled. In such a system, the ability of the fermentation organism to produce ethanol is affected by the ethanol and sugar concentrations. As a rule, a yeast which gives high conversion rates of sugar to ethanol in a low-ethanol, high-sugar fermentation medium will only sluggishly produce ethanol under the opposite conditions, i.e., at high-ethanol level, low-sugar concentrations.

Accordingly, there has heretofore existed a need for a process of rapid continuous fermentation of fermentable sugar such as that derived from the hydrolysis of manioc root starch to provide industrial ethanol at competitive prices.

SUMMARY OF THE INVENTION

In accordance with the present invention, an aqeuous solution of fermentable sugar, advantageously one which has been prepared by the starch hydrolysis process of commonly assigned copending U.S. patent application Ser. No. 043,191, filed May 29, 1979, is continuously subjected to fermentation in a series of fermentation vessels in which the ethanol content of the fermentation medium is progressively increased as the sugar content of the fermentation medium is consumed by the yeast. At least two strains of yeast are selected for the fermentation, one of which provides a high rate of ethanol production in a fermentation medium containing a relatively low concentration of ethanol and a relatively high concentration of fermentable sugar and the other of which provides a high rate of ethanol production in a fermentation medium containing a relatively high concentration of ethanol and a relatively low concentration of fermentable sugar. The process also contemplates the adjustment of temperature and/or pH in each fermentation vessel as required to maintain optimum fermentation activity therein. To conserve raw materials and direct yeast metabolic activity to the production of ethanol rather than cell growth and propagation, a portion of the yeast is continuously recycled and additional fresh yeast is added only as is necessary to replace dead cells.

The aqueous ethanol or "beer" containing as much as about 12 weight percent ethanol which is obtained by the foregoing process can be concentrated employing any of the known and conventional techniques and is advantageously concentrated by the anhydrous distillation process disclosed in commonly assigned copending U.S. patent application Ser. No. 043,189, filed May 29, 1979. The stillage effluent obtained from the rectifying column employed in the aforesaid anhydrous distillation process contains soluble proteins and amino acids of the original beer feed and provides an excellent source of nutrient for yeast employed in the fermentation process herein.

Employing two or more organisms which maintain high rates of ethanol production in the presence of different concentrations of ethanol and fermentable sugar provides a faster, more efficient fermentation than that attainable employing a single strain of yeast in each fermentation vessel as is the current practice. As such, the fermentation process of this invention is particularly well suited for the production of ethanol which is price competitive with ethanol produced from non-vegetative sources.

The term "fermentable sugar" should be understood as referring to a single fermentable sugar as glucose (dextrose), fructose, maltose or sucrose but more commonly will be applicable to these and similar fermentable saccharides in admixture.

BRIEF DESCRIPTION OF THE DRAWING

The accompanying drawing is a diagrammatic flow sheet illustrative of one embodiment of an ethanol fermentation process in accordance with the present invention.

DESCRIPTION OF THE PREFERRED EMBODIMENTS

Referring to the drawing, a sterile aqueous solution of fermentable sugar from any source containing from about 10 to about 40 weight percent sugar, and preferably from about 15 to about 25 weight percent sugar, is taken from vessel 50 which can be a storage vessel or a saccharification vessel in which the sugar is obtained by the hydrolysis of liquefied starch, and is delivered by pump 51 through line 52 to a first temperature regulated, agitated fermentation vessel 53 provided with pH control and means for introducing nutrients and the small amounts of oxygen conventionally employed for maintaining proper yeast metabolism during fermentation. In the event the sugar solution contains more than 20 weight percent sugar, it is preferable to dilute the solution to about this level of sugar, advantageously with the nitrogen-rich stillage obtained from an ethanol distillation unit such as described in the aforesaid Ser. No. 043,189, filed May 29, 1979. The use of stillage when available possesses the two-fold advantage of recycling nitrogen to the fermentation system which would otherwise be lost upon concentration of the ethanol during distillation, and reducing process water consumption by avoiding water build-up in the still bottoms. In addition to sugar, the foregoing solution may also contain significant amounts of partial starch hydrolysates (e.g., up to about 40 weight percent of the total carbohydrate present) which can be saccharified to fermentable sugar under the influence of the saccharifying enzyme produced by the fermenting yeast and/or added saccharifying enzyme. A pumpable slurry of ethanol-producing yeast organisms free of contaminating organisms is conveyed from yeast storage tank 54 by pump 55 through lines 56 and 57 into fermentation vessel 53. The yeast selected for introduction in fermentation vessel 53 is one which provides high rates of ethanol production in the presence of relatively low concentrations of ethanol and relatively high concentrations of fermentable sugar. Yeasts which will perform in this manner can be selected employing known microbiological techniques. Thus, for example, several strains of yeast can be introduced into a laboratory or large scale fermentation vessel (e.g., a chemostat) in which initial ethanol, sugar and nutrient concentrations are noted and predetermined levels of temperature and pH are accurately maintained so as to simulate the conditions present in a commercial fermentation unit. As the different strains of yeast compete with one another for survival over a prolonged period which can be several weeks or even months, only one or a few strains will have survived, the surviving organisms being optimal producers of ethanol under the conditions selected for the operation of the fermentation unit. Using the same procedure, the mutation of a single yeast organism to provide an optimal ethanol producer under the fermentation conditions selected can be induced. The foregoing screening procedure can also be used to evaluate and isolate selected strains of yeast produced by techniques of induced mutation, e.g., those employing ultraviolet radiation, gamma rays, etc. to accelerate the incidence of mutation. Other useful techniques for obtaining different strains of yeast for evaluation as ethanol producers under predetermined fermentation conditions include cross breeding of two different strains to yield a third and genetic engineering in which genetic materials from two different strains are recombined to form a completely new genetic "blueprint". A yeast which has been found to provide especially good rates of ethanol production at relatively low concentrations of ethanol and relatively high concentrations of fermentable sugar is *Saccharomyces bayanus*. The yeast in fermentation vessels 53 and 67 can be present at a level of from about 2 to about 8 weight percent of the fermentation medium (based on dry weight of yeast) and preferably is present at from about 3 to about 6 weight percent. Once continuous fermentation has started and a steady state has been achieved, there will be no need to add more yeast other than those amounts necessary to make up for cells which die. The temperature of each fermentation vessel is advantageously regulated at a level which favors maximum ethanol production, i.e., generally from about 68° F. to about 104° F. and preferably from about 86° F. to about 99° F. The pH of each fermentation vessels is similarly regulated and can range from about 3.5 to about 5.5 and preferably from about 4.0 to 4.6. Dilute ethanol produced in fermentation vessel 53 containing a portion of the yeast cells therein is conveyed by pump 58 through line 59 to yeast separator/recovery unit 60 which separates substantially all of the yeast cells from the aqueous ethanol stream. Unit 60 can be a micro-filtration device, centrifuge, etc. Since fermentation is exothermic, a portion of the fermentation medium passing through line 59 is diverted through line 61 into cooler 62 and returned to fermentation vessel 53. The yeast cells recovered in unit 60 are conveyed as a pumpable slurry or "cream" containing from about 10 to about 50 weight percent dry yeast and preferably from about 20 to 40 weight percent dry yeast by pump 63 through lines 64 and 57 into fermentation vessel 53. The ethanol-containing fermentation medium thus freed of yeast cells is delivered by pump 65 through line 66 into fermentation vessel 67 which is essentially similar to fermentation vessel 53. A pumpable slurry of ethanol-producing yeast organisms essentially free of contaminating organisms is conveyed from yeast storage tank 68 by pump 69 through lines 70 and 71 into fermentation vessel 67. The yeast selected for introduction in fermentation vessel 67 is one which provides high rates of ethanol production in the presence of relatively high concentrations of ethanol and relatively low concentrations of fermentable sugar. Strains of yeast satisfying these requirements can be isolated in the manner described above. A yeast which has been found to provide especially good rates of ethanol production at relatively high concentrations of ethanol and relatively low concentrations of fermentable sugar is *Saccharomyces cerevisiae* (Distillers Active Dry Yeast from Red Star Yeast). The dilute aqueous ethanol (approximately 10 to 12 weight percent ethanol) containing yeast cells is withdrawn from fermentation vessel 67 and conveyed by pump 72 through line 73 to yeast separator/recovery unit 74. A portion of the fermentation medium passing through line 73 is diverted through line 75 into cooler 76 and returned to fermentation vessel 67. The yeast cells recovered in unit 74 are conveyed as a pumpable slurry (similar in fluid characteristics to the yeast slurry recovered from unit 60) by pump 77 through lines 78 and 71 to fermentation vessel 67. The cell-free ethanol solution from yeast separator/recovery unit 74 is delivered by pump 79 through line 80 directly to an ethanol concentration unit, e.g., anhydrous distillation apparatus, and/or to a storage facility. It is also within the scope of this invention to employ both types of yeast herein in such fermentation vessel with only one yeast separation/recovery unit (receiving the fermentation medium from the last fermentation vessel in the series) being provided. Metabolically evolved carbon dioxide gas containing ethanol is conveyed from each of fermentation vessels 53 and 67 through common line 81 and by means of blower 82 is introduced into the bottom of ethanol absorption unit 83. Water at ambient temperature entering the top of the absorption unit through line 84 and flowing downwardly, absorbs substantially all of the ethanol vapor rising through the unit. The aqueous solution of ethanol withdrawn from the base of ethanol absorption unit 83 through line 85 is conveyed to line 80 where it is combined with the bulk of the flow from the last fermenter. Vent gases are discharged from ethanol absorption unit 83 through atmospheric vent line 86.

What is claimed is:

1. A process for the production of ethanol by continuous fermentation which comprises carrying out fermentation upon an aqueous solution of fermentable sugar in a series of fermentation vessels in which the ethanol content of the fermentation medium is progressively increased in each fermentation vessel as the fermentable sugar is consumed therein, the fermentation employing at least two different strains of ethanol-producing yeast, one of which provides a high rate of ethanol production in a fermentation medium containing a relatively low concentration of ethanol and a relatively high concentration of sugar and the other of which provides a high rate of ethanol production in a fermentation medium containing a relatively high concentration of ethanol and a relatively low concentration of fermentable sugar.

2. The process of claim 1 wherein the aqueous solution of fermentable sugar contains partial starch hydrolysate in an amount of up to about 40 weight percent of the total carbohydrate present, the partial starch hydrolysate undergoing saccharification to fermentable sugar under the influence of saccharifying enzyme produced by the yeast and/or added saccharifying enzyme.

3. The process of claim 1 wherein the strain of yeast which provides a high rate of ethanol production in a fermentation medium containing a relatively low concentration of ethanol and a relatively high concentration of sugar is *Saccharomyces bayanus*.

4. The process of claim 1 wherein the strain of yeast which provides a high rate of ethanol production in a fermentation medium containing a relatively high concentration of ethanol and a relatively low concentration of sugar is *Saccharomyces cerevisiae*.

5. The process of claim 1 wherein each different strain of yeast is separately employed in a fermentation vessel and is separately recovered therefrom and recycled thereto.

6. The process of claim 1 wherein the different strains of yeast are used together in each fermentation vessel and are separated from the last fermentation vessel in the series and recycled to the first fermentation vessel in the series.

7. The process of claim 1 wherein ethanol contained in the carbon dioxide gas evolved during fermentation is recovered.

8. The process of claim 1 wherein from 2 to 8 weight percent of yeast calculated on a dry yeast basis is present in each fermentation vessel.

9. The process of claim 8 wherein from 3 to 6 weight percent of yeast calculated on a dry yeast basis is present in each fermentation vessel.

10. The process of claim 1 wherein the aqueous solution of fermentable sugar contains from about 10 to about 40 weight percent sugar.

11. The process of claim 10 wherein the aqueous solution of fermentable sugar contains from about 15 to 25 weight percent sugar.

* * * * *